United States Patent
Bertoch et al.

(10) Patent No.: US 6,533,761 B2
(45) Date of Patent: Mar. 18, 2003

(54) CATHETER SECURING DEVICE AND BITE BLOCK

(75) Inventors: Todd M. Bertoch, APO, AP 96326; Ted F. Gingrich, San Antonio, TX (US); Steven C. Walker, Baldwin, MO (US); John M. Shepherd, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/867,768

(22) Filed: May 31, 2001

(65) Prior Publication Data

US 2002/0095118 A1 Jul. 18, 2002

Related U.S. Application Data

(60) Provisional application No. 60/208,067, filed on May 31, 2000.

(51) Int. Cl.$^7$ .......................... A61M 5/32; A61M 29/00; A62B 18/08
(52) U.S. Cl. .................. 604/174; 606/196; 128/206.29; 128/DIG. 26
(58) Field of Search ............................ 604/77, 79, 174, 604/179; 606/196; 128/DIG. 26, 207.17, 206.29

(56) References Cited

U.S. PATENT DOCUMENTS

| 2,521,084 A | 8/1950 | Oberto ........................ 128/141 |
| 2,669,988 A | 2/1954 | Carpenter ................... 128/136 |
| 2,693,182 A | 11/1954 | Phillips |
| 2,820,457 A | 1/1958 | Phillips |
| 2,882,893 A | 4/1959 | Godfroy ...................... 128/136 |
| 2,908,269 A | 10/1959 | Cheng |
| 3,602,227 A | 8/1971 | Andrew |

(List continued on next page.)

FOREIGN PATENT DOCUMENTS

| WO | WO 01/58349 A1 | 8/2001 |
| WO | WO 01/62325 A1 | 8/2001 |

*Primary Examiner*—Brian L. Casler
*Assistant Examiner*—Catherine Serke
(74) *Attorney, Agent, or Firm*—Elizabeth Arwine

(57) ABSTRACT

A device for securing a catheter with respect to a patient's mouth that preferably includes a balloon that can be inflated within the patient's mouth on the exterior of the catheter, a bite block, and a shield. The balloon preferably immobilizes the catheter with respect to the securing device when inflated while permitting relative movement of the catheter and the securing device when deflated. The balloon preferably also prevents inadvertent withdrawal of the securing device from the patient's mouth when inflated while permitting withdrawal when deflated. The invention preferably includes a method for using such a securing device.

19 Claims, 3 Drawing Sheets

U.S. PATENT DOCUMENTS

| | | | |
|---|---|---|---|
| 3,760,811 A | 9/1973 | Andrew | |
| 3,774,616 A | 11/1973 | White et al. | |
| 3,908,665 A | 9/1975 | Moses | 128/351 |
| 4,112,936 A | 9/1978 | Blachly | 128/136 |
| 4,198,970 A | 4/1980 | Luomanen | 128/208 |
| 4,205,819 A | 6/1980 | Soika | |
| 4,222,391 A | 9/1980 | Rawson et al. | 128/736 |
| 4,270,529 A | 6/1981 | Muto | |
| 4,270,531 A | 6/1981 | Blachly | 128/207.14 |
| 4,351,330 A * | 9/1982 | Scarberry | 128/207.15 |
| 4,351,331 A | 9/1982 | Gereg | |
| 4,392,857 A | 7/1983 | Beran | |
| 4,425,911 A | 1/1984 | Luomanen et al. | 128/200.26 |
| 4,495,945 A | 1/1985 | Liegner | 128/200.26 |
| 4,502,478 A | 3/1985 | Lifton | 128/136 |
| 4,530,354 A | 7/1985 | Froilan | |
| 4,640,273 A | 2/1987 | Greene et al. | 128/136 |
| 4,676,240 A | 6/1987 | Gardy | 128/207.14 |
| 4,683,882 A | 8/1987 | Laird | |
| 4,699,616 A | 10/1987 | Nowak et al. | 604/180 |
| 4,744,358 A * | 5/1988 | McGinnis | 128/207.17 |
| 4,774,944 A | 10/1988 | Mischinski | |
| 4,791,941 A | 12/1988 | Schaefer | 128/861 |
| 4,944,313 A | 7/1990 | Katz et al. | 128/859 |
| 5,026,352 A | 6/1991 | Anderson | 604/178 |
| 5,069,206 A | 12/1991 | Crosbie | 128/207.17 |
| 5,123,410 A | 6/1992 | Greene et al. | 128/207.17 |
| 5,174,284 A | 12/1992 | Jackson | 128/200.26 |
| 5,193,544 A | 3/1993 | Jaffe | 128/634 |
| 5,205,281 A | 4/1993 | Buchanan | 128/207.14 |
| 5,282,464 A | 2/1994 | Brain | 128/207.15 |
| 5,305,742 A | 4/1994 | Styers et al. | |
| 5,318,017 A | 6/1994 | Ellison | 128/200.24 |
| 5,320,097 A | 6/1994 | Clemens et al. | |
| 5,355,874 A | 10/1994 | Bertram | 128/200.26 |
| 5,402,776 A * | 4/1995 | Islava | 128/207.14 |
| 5,413,095 A | 5/1995 | Weaver | 128/200.26 |
| 5,501,216 A | 3/1996 | Byrd | |
| 5,529,062 A * | 6/1996 | Byrd | 128/200.26 |
| 5,551,421 A | 9/1996 | Noureldin et al. | |
| 5,626,128 A | 5/1997 | Bradley et al. | |
| 5,655,519 A | 8/1997 | Alfrey | 128/200.26 |
| 5,715,816 A | 2/1998 | Mainiero et al. | 128/633 |
| 5,746,202 A | 5/1998 | Pagan | 128/207.14 |
| 5,782,236 A | 7/1998 | Ess | 128/207.17 |
| 5,803,079 A | 9/1998 | Rogers | 128/207.14 |
| 5,806,516 A * | 9/1998 | Beattie | 128/207.14 |
| 5,829,430 A | 11/1998 | Islava | 128/200.26 |
| 5,894,840 A | 4/1999 | King | |
| 6,244,865 B1 | 6/2001 | Nelson et al. | 433/140 |
| 2002/0092526 A1 | 7/2002 | Bertoch et al. | |
| 2002/0095119 A1 | 7/2002 | Bertoch et al. | |

* cited by examiner

CATHETER SECURING DEVICE AND BITE BLOCK

This application claims the benefit of U.S. provisional Application Serial No. 60/208,067, filed May 31, 2000, which is hereby incorporated by reference.

I. FIELD OF THE INVENTION

This invention relates to a device for securing a catheter with respect to a patient's mouth while also preventing occlusion of the catheter when the patient's jaw closes. Furthermore, the invention may be used both in human medicine and veterinary medicine.

II. BACKGROUND OF THE INVENTION

Catheters are employed for many purposes to provide for passage of fluids, including gases, to and from the human body. One type of catheter is an endotracheal tube, which is adapted to be inserted through the oral cavity of a patient and into the trachea to provide for the supply of fluids to the body, for the monitoring of internal conditions in the body and/or to provide for removal of secretions from within the body.

It is desirable to secure the catheter in place within the patient to prevent the catheter from being inadvertently mainstem intubated (advanced into the patient) or extubated (retracted (or removed) from the patient's mouth) after it has been properly positioned; however, it is difficult to properly secure catheters to a patient's face to prevent these events. Neck straps are effective for holding catheters, but the neck straps can often hinder jugular venous flow or impede line placement within the patient. Tapes and adhesives are ineffective routinely, because of the presence of facial hair, dirt, blood, debris, perspiration, excessive soft tissue or facial trauma.

Another problem is that the catheter is usually relatively easy to deform and passes between the patient's teeth if inserted orally. Thus, it is desirable to prevent the lumen of the catheter from being occluded by a patient's teeth when the patient attempts to bite down. Occlusion of the catheter can lead to, for example, hypoxia, hypercarabia, and the syndrome known as negative pressure pulmonary edema. The various restraining approaches discussed above are ineffective in protecting against possible occlusion of the catheter. Bite blocks can be effective in keeping a patient's jaw open and thus prevent the teeth from clamping down on the catheter. The problem is that the bite block is yet another piece of equipment that may be inserted into the patient's mouth along with a securing device and other medical apparatuses including, for example, multiple hoses/tubes and pulse oximeter sensors.

Notwithstanding the above devices, a need still exists for an apparatus to secure a catheter inserted orally in place at a desired depth within the patient while also preventing the patient from occluding the inserted catheter.

III. SUMMARY OF THE INVENTION

The present invention provides a securing device for a catheter that secures the catheter in the patient's mouth to prevent inadvertent extubation or mainstem intubation. The present invention also provides a securing device with a bite block that prevents occlusion of the lumen of the catheter by a patient's teeth. The present invention further provides a method of protecting and securing the catheter and a method of intubation.

According to one aspect of the present invention, a device for securing a catheter with respect to a patient's mouth preferably includes a bite block having a distal end and a proximal end, a balloon attached to the distal end of said bite block, and a shield extending from the proximal end of said bite block.

According to one aspect of the present invention, a device for securing the catheter with respect to a patient's mouth preferably includes a shield for positioning on an exterior of a patient's mouth for limiting a distance by which the securing device can be inserted into the patient's mouth and having an opening through which the catheter can pass; a bite block connected to the shield for insertion into the patient's mouth between the patient's teeth to protect the catheter against occlusion by the patient's teeth; and a balloon having a passageway through which the catheter can pass, a first portion disposed in the bite block, and a second portion disposed outside the bite block, the balloon having a deflated state in which the catheter may pass freely through the bite block and an inflated state in which the first portion of the balloon presses against the catheter to resist lengthwise movement of the catheter with respect to the bite block and the second portion can contact an interior surface of the patient's mouth to resist withdrawal of the securing device from a patient's mouth.

According to one aspect of the present invention, a method for intubating a patient through an oral cavity preferably includes sliding a securing device having a balloon, a bite block, and a shield over a catheter to a point near a proximal end of the catheter, inserting a distal end of the catheter into the patient through the oral cavity, positioning the securing device such that the balloon is within the oral cavity of the patient, the bite block is between an upper jaw and a lower jaw of the patient, and the shield is external to the patient, and inflating the balloon such that is frictionally holds in place the catheter at a depth desired and fills a portion of the oral cavity such that the securing device will resist being removed from the patient.

According to one aspect of the present invention, a device for securing a catheter to a patient when the catheter is inserted into a mouth of the patient preferably includes means for resisting insertion of the entire device into the mouth of the patient, means for preventing occlusion of the catheter by the patient, means for gripping the catheter, and means for selectively resisting removal of the device from the mouth of the patient.

An objective of the invention is to securely hold a catheter at a set depth within the patient as set by a medical professional.

Another objective of the invention is to prevent occlusion from occurring within the lumen of a catheter when the patient bites down on the catheter.

Another objective of the invention is to provide a multi-functional tool for use with patients.

A further objective of the invention is to provide a device that can be used in the operating room, the intensive care unit (ICU), the emergency room, or the field in any situation that requires a quick, easy, and reliable means of securing a respiratory tube or a catheter.

Yet another objective of the invention is to still have access to the oral cavity of the patient for other medical devices.

An advantage of the invention is that a catheter is securely held at a constant insertion depth when set by a medical professional, at least in part because of the balloon and the shield working together.

Another advantage of the invention is that it can still work when debris, blood, facial hair, dirt, perspiration, excessive soft tissue and facial trauma are present in the vicinity and even within the oral cavity.

Another advantage of the invention is that a catheter is protected from occlusion resulting from forces being applied by the patient's jaw and teeth.

Another advantage of the invention is the minimization and elimination of the likelihood of inadvertent extubation or mainstem intubation.

Another advantage of the invention is the inclusion of two different devices within one device.

A further advantage of the invention is that it may work with all patients requiring endotracheal, laryngeal mask, or combitube intubation.

Further features and advantages of the present invention, as well as the structure and operation of various embodiments of the present invention, are described in detail below with reference to the accompanying drawings.

IV. BRIEF DESCRIPTION OF THE DRAWINGS

The present invention is described with reference to the accompanying drawings. In the drawings, like reference numbers indicate identical or functionally similar elements or steps. The use of cross-hatching within the drawings is not intended as limiting the type of materials that may be used to manufacture the invention.

Figure 5A:
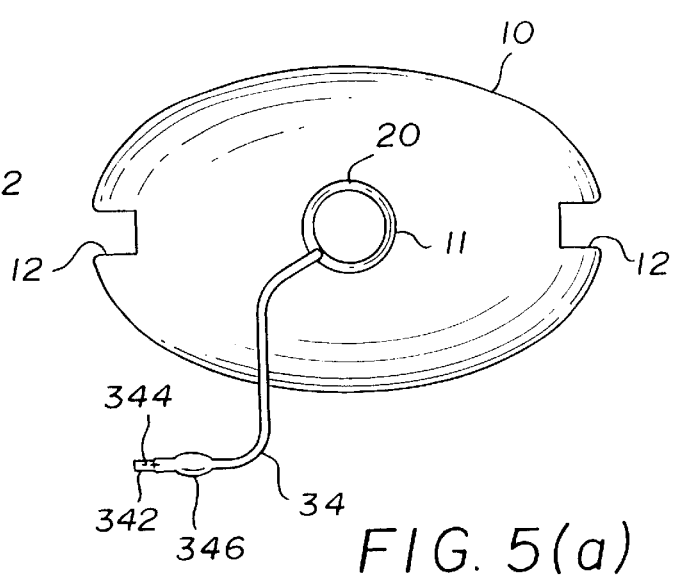
Figure 5B:
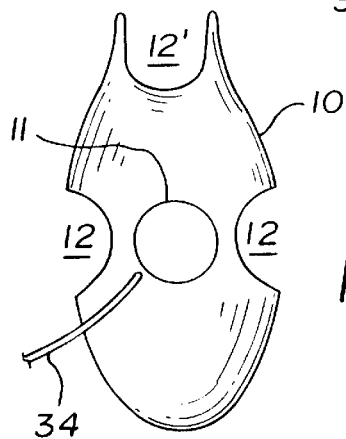

FIGS. 5(a)–(b) illustrate a front elevation of another embodiment according to the invention.

Figure 6:
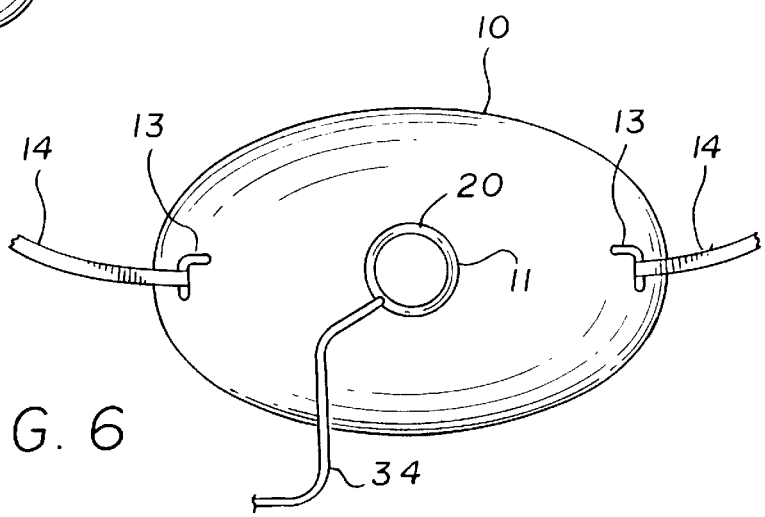

FIG. 6 depicts a front elevation of another embodiment according to the invention.

Figure 7:
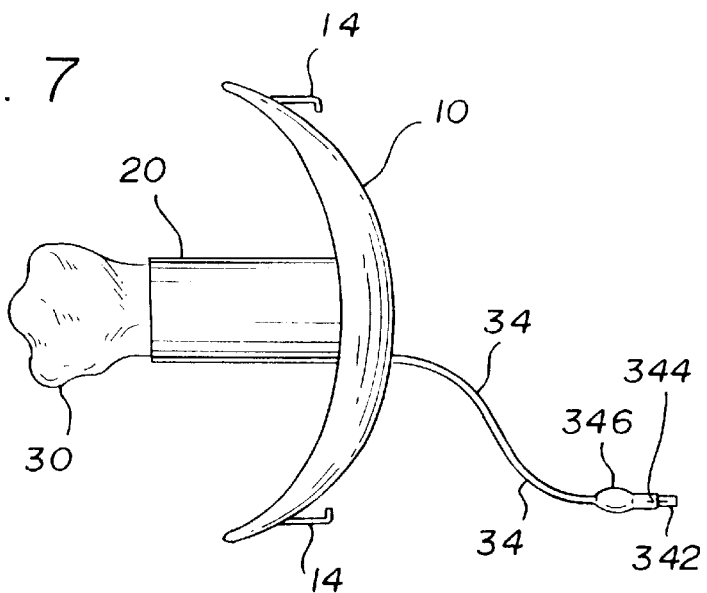

FIG. 7 illustrates a top view of another embodiment according to the invention.

Figure 8:
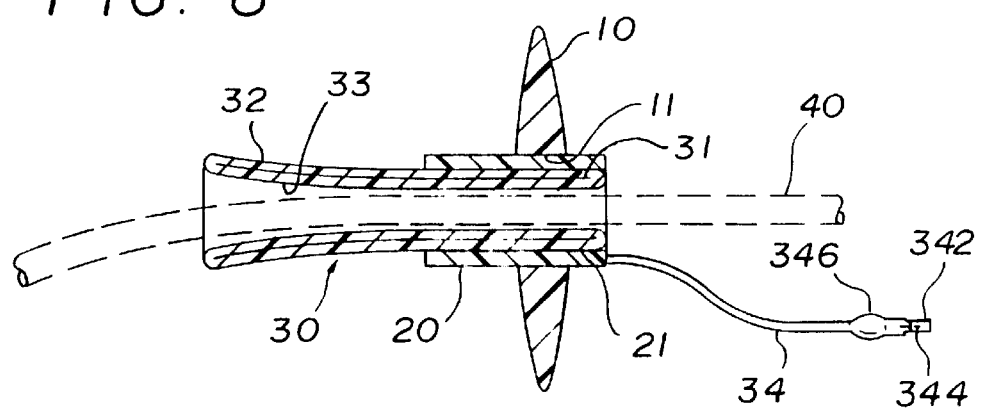

FIG. 8 depicts a cross-sectional side view of another embodiment according to the invention.

Figure 9:
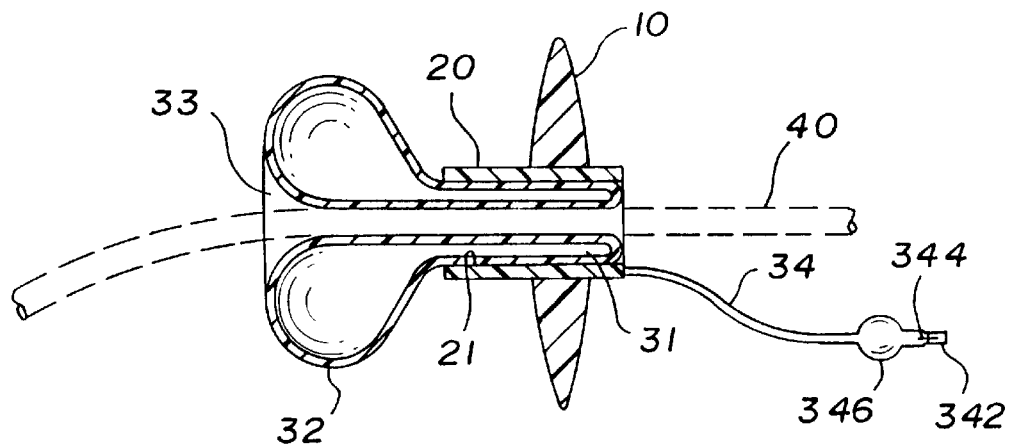

FIG. 9 illustrates a cross-sectional side view of the embodiment depicted in FIG. 8 with the balloon in an inflated state.

V. DETAILED DESCRIPTION OF THE INVENTION

A preferred embodiment of a securing device according to the present invention will be described with reference to FIGS. 1–4. The illustrated embodiment will be described for use in securing a catheter such as an endotracheal tube.

The preferred embodiment includes a shield 10 to be positioned on an exterior of a patient's mouth to prevent the securing device from completely entering into a patient's mouth, a bite block 20 connected to the shield 10 for preventing a catheter 40 such as the endotracheal tube (shown in phantom, for example, in FIGS. 2 and 3) held by the securing device from being occluded by the patient's teeth, and a balloon 30 that can be inflated within the patient's mouth around the exterior of the catheter 40. The shield 10 preferable rings or abuts the bite block 20. The bite block 20 preferably is connected to the balloon 30 such that the balloon 30 inflates away from the bite block 20 to fill the oral cavity of the patient as illustrated, for example, in FIGS. 1–3. Preferably, the balloon 30 provides an enclosed passageway for the catheter 40 to pass through.

The shield 10 preferably is any member having outer dimensions large enough to prevent the shield 10 from entering the oral cavity of the patient's mouth, whereby the catheter 40 to which the shield 10 is attached can be prevented from being inadvertently advanced into the patient resulting in mainstem intubation after it has been properly positioned. The shape of the shield 10 is not critical. The shield 10 preferably is a plate-like member with a thickness, which is small relative to its height and width. Preferably, the shield 10 has an oblong shape with a length in the widthwise direction of a patient's mouth that is greater than its height. An opening 11 through which the catheter 40 can pass preferably is formed through the thickness of the shield 10, and more preferably the opening 11 is centered on the front surface of the shield 10.

The bite block 20 preferably is any member which can prevent the patient from occluding with his teeth the catheter 40 passing through the shield 10, because occlusion may result in hypoxia, hypercarbia, a negative pressure pulmonary edema, or similar problems. The bite block 20 preferably is a body of revolution having a straight longitudinal bore (or passageway or channel) 21 at its axial center that is aligned with the opening 11 in the shield 10 or the bite block 20 may fit within the shield opening 11. Alternatively, since the patient's teeth will typically be able to exert a force on the catheter 40 only in a limited direction, the bite block 20 need not extend around the entire periphery of the catheter 40.

The balloon 30 may be secured to one of the other components of the securing device to prevent the balloon 30 from becoming detached from the bite block 20 when a force is applied to the catheter 40 in its lengthwise direction. For example, the balloon 30 can be bonded and/or attached to a distal end of the bite block 20.

The balloon 30 can serve a number of functions. One function is to press radially inwardly against the outer surface of the catheter 40 to prevent advancement or withdrawal of the catheter 40 into or out of the patient once the balloon 30 is inflated as illustrated, for example, in FIG. 3. Another function that the balloon 30 can perform is to resist forces tending to pull the securing device and the catheter 40 out of the patient's mouth. The balloon 30 preferably accomplishes both of these functions.

The balloon 30 preferably includes a central bore (or passageway) 33 for receiving the catheter 40 such that the balloon 30 can be inflated around the bore 33 by introducing an inflating fluid into the balloon 30 through an inflating line 34, which can be connected to an unillustrated inflating fluid source. The inflating line 34 preferably will pass through an enclosed channel (not shown) running longitudinally within the bite block 20 to reach the balloon 30. Balloon 30 is not constrained against outward expansion, so when it is inflated, it swells to contact the hard palate and the lingual surface of the patient's mouth. In this state, the balloon 30 prevents the securing device as a whole from being inadvertently pulled out of the patient's mouth, and since the catheter 40 is engaged by the balloon 30, the catheter 40 is prevented from moving with respect to the securing device.

Preferably, when the balloon 30 is inflated, the balloon 30 has an oblong shape with a height in the height direction of a patient's mouth which is greater than its width in the widthwise direction of the patient's mouth. However, the balloon 30 can have many other shapes in its inflated state, such as the shape of a sphere or other body of revolution. The balloon 30 need not have a special structure. For example, it may be a commercially available balloon of the type generally used for catheters such as endotracheal tubes to hold endotracheal tubes in place within the trachea. The balloon 30 preferably will be relatively inelastic (like those of a plastic bag) which undergo little stretching when the balloon 30 is inflated, alternatively the balloon 30 may have highly elastic walls that stretch as the balloon 30 is inflated.

The inflating fluid preferably is either a gas or a liquid, although a gas may be more preferable from the standpoint of patient comfort since it is less dense. Furthermore, a gas may be easier to use than a liquid, since a gas can be simply vented to the atmosphere when the balloon 30 is deflated rather than having to be collected. The balloon 30 preferably will be inflated with a low pressure.

Figure 1:
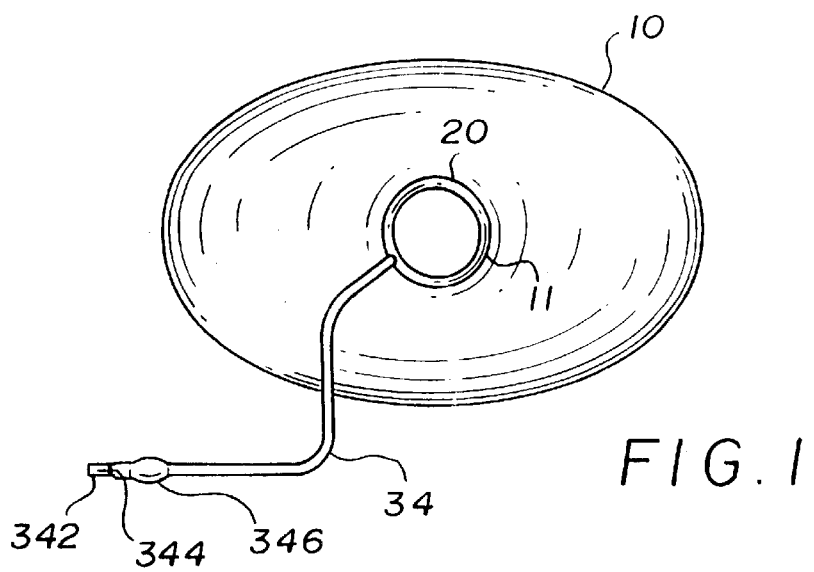
FIG. 1 illustrates a front elevation of a preferred embodiment according to the invention.
Figure 2:
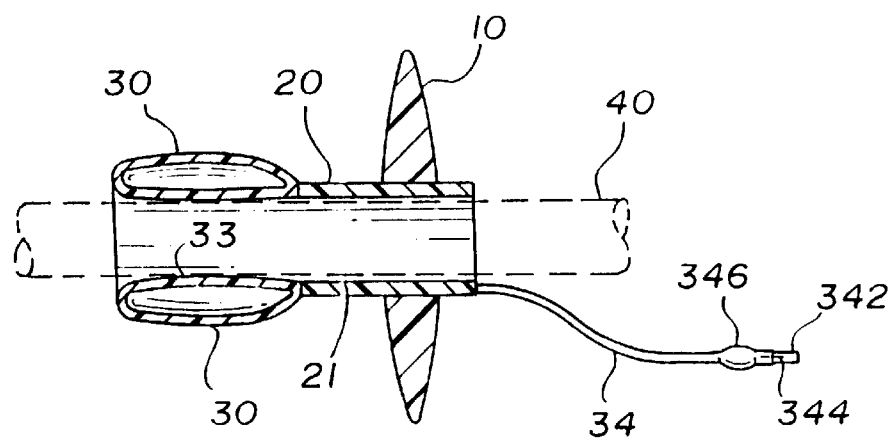
FIG. 2 depicts a cross-sectional side view of the embodiment of FIG. 1 with a balloon of the securing device in a deflated state.
Figure 3:
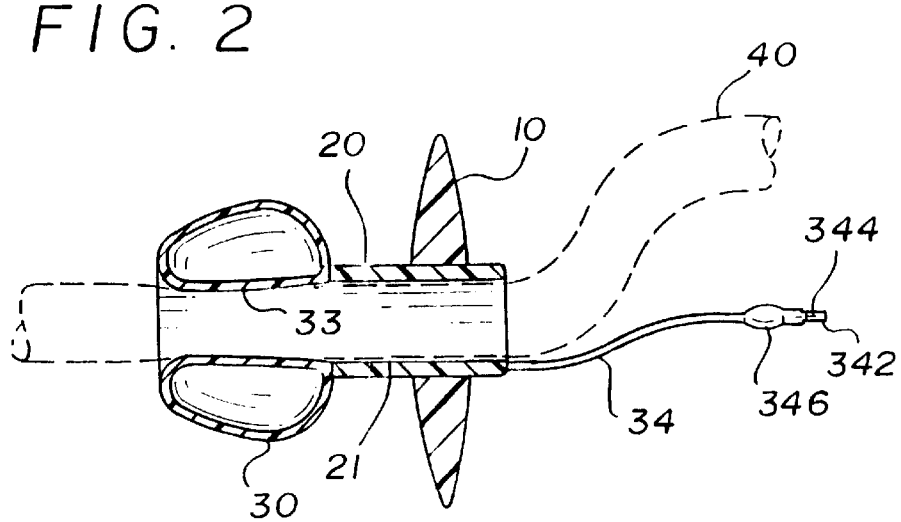
FIG. 3 illustrates a cross-sectional side view of the embodiment of FIG. 1 with the balloon in an inflated state.
Figure 4:
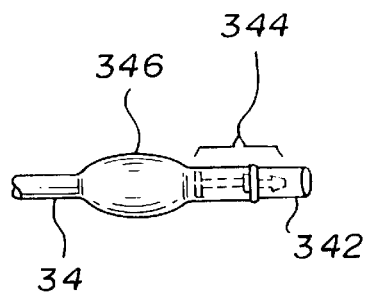
FIG. 4 depicts an enlarged view of a proximal end of a fluid line according to the invention.

Preferably, the inflating line 34 will include a fitting at its proximal end to connect to a variety of attachments including syringes or other devices that preferably can deliver measure doses to act as a built-in safety feature to prevent over expanding the balloon 30. The fitting preferably will include a connector 342 to provide versatility in items capable of attaching to the fluid line 34, a spring valve 344, and a status balloon 346 as illustrated in FIG. 4. The connector 342 preferably is either a friction connector or a luer-lock (not shown). The spring valve 344 preferably is of the type that when the fluid provider is attached to the connector 342 the spring valve 344 will be pushed into the fluid line 34 and open a passage for the fluid to travel through to reach the balloon 30. Preferably, after the spring valve 344, the status balloon 346 will be situated to provide a visual indication as to whether the balloon 30, which will be within the patient's oral cavity, is filled with fluid as the status balloon 346 preferably will mirror the inflation state of the balloon 30. Alternatively, the status balloon 346 may be eliminated. Preferably, the inflating fluid is air such as that pumped from a syringe.

The shield 10 and the bite block 20 can be made of a wide variety of materials, including plastics. The shield 10 and the bite block 20 preferably are made of at least one of the following: polypropylene, polyvinyl chloride, silicones, epoxies, polyester, thermoplastics, rubber, similar flexible material, etc. More particularly the shield 10 may be made of same material used to manufacture pacifier shields.

The shield 10 and the bite block 20 may be separately formed and then secured to each other, or they may be integrally formed with each other, depending upon the materials of which they are made. Preferably, the bite block 20 may abut the shield 10 such that the opening 11 is aligned with and able to communicate with the bore 21. Alternatively, the bite block 20 extends through the opening 11 in the shield 10 and is secured to the shield 10 by bonding, for example, if not integrally form with the shield 10. Another alternative embodiment is that the shield 10 is spaced from the proximal end of the bite block 20. It may be convenient if one or both of the shield 10 and the bite block 20 is made of a see-through material, such as a transparent plastic, to enable the condition of a patient's mouth and nostrils, of the catheter 40, or of the balloon 30 to be readily observed for obstructions, contamination, or damage.

An alternative embodiment adds one or more cutouts, slots, holes, or openings (means for allowing the insertion of medical instruments) 12 to the shield 10 as illustrated in FIGS. 5(a)–(b) that allow, for example, instruments, tubes, or monitoring equipment to be inserted into and through the oral cavity such as oral gastric tubes or an esophageal stethoscope, or pulse oximeter sensors. In the illustrated alternative embodiment, the openings 12 are formed in the periphery of the shield 10 at opposite widthwise ends thereof, but the openings 12 may be formed in other locations. The openings 12 may also serve as drainage holes (or relief openings) for spit and saliva that might build up in the oral cavity. Another alternative embodiment is for the shield 10 to have a cutout 12' at the top so that the patient's nose will not be covered as illustrated in FIG. 5(b). This alternative embodiment is particularly useful if the shield has sufficient height to approach the nose of an average sized patient. A still further alternative is for the shield to include a mesh pattern over at least a portion of it.

Another alternative embodiment for the shield 10 is a structure for enabling it to be secured to the exterior of a patient's head as illustrated, for example, in FIGS. 6 and 7. The shield 10 may include a pair of hooks (or eyelets or handles) 13, which preferably are on opposite widthwise ends (or sides). Each of the hooks 13 preferably can be connected to an end of a strap 14 that may be, for example, an elastic band, a string, or other member that can go around the back of the patient's head or neck to hold the shield 10 in place. The strap 14 can be relatively loose and need not cause the patient any discomfort, since the shield 10 is also held in place by the balloon 30. Alternatively, the hooks 13 may be integrally formed with the shield 10, for example, on the edge/periphery of the shield 10 or spaced from the edge/periphery of the shield 10 (FIG. 6 illustrates such spacing).

A further alternative embodiment for the shield is illustrated in FIG. 7, which is a top view of this alternative embodiment. The shield 10 preferably is curved to fit the average human jaw. An advantage of this is that a lower profile will be provided by the securing device to the patient's face.

Another alternative embodiment for the balloon 30 is to have two portions that include a first portion 31 that is disposed within the bore (or passageway) 21 of the bite block 20 and a second portion 32 (described in the preferred embodiment as the balloon 30) that is disposed at or about the distal end of the bite block 20 (the end which extends furthest into a patient's mouth) as illustrated in FIGS. 8 and 9.

The bore 21 of the bite block 20 is preferably sufficiently large that when the first portion 31 of the balloon 30 is not inflated, the catheter 40 can pass easily through the bore 21 such that the position of the catheter 40 may be adjusted in its lengthwise direction with respect to the securing device. When the balloon 30 is inflated, the first portion 31 of the balloon 30 is constrained against outward expansion by the bite block 20, so it expands radially inwardly to snugly contact the outer wall of the catheter 40 and thereby prevent the catheter 40 from moving in its lengthwise direction with respect to the bite block 20.

The bore 21 of the bite block 20 may be selected so as to be able to accommodate catheters 40 having a wide range of diameters. The first portion 31 of the balloon 30 can be expanded inwardly by a larger amount to contact the outer surface of catheters 40 having a small diameter, and it can be expanded inwardly by a smaller amount to contact the outer surface of catheters 40 having a large diameter, thus automatically adjusting to the diameter of the catheter 40. As a result, one securing device can be used for many different sized catheters 40.

Instead of there being a single balloon 30, the two portions 31 and 32 of the balloon 30 may be replaced by separate balloons, which may be inflated together preferably using the same fluid line 34 or individually with each balloon portion preferably having its own fluid line 34. The use of separate balloons on the inside and outside of the bite block 20 permits more precise control of the size and pressure of each balloon. For example, there may be cases in which it is desired to inflate a balloon within the bite block 20 to hold the catheter 40 in place, but in which it is preferable not to inflate a balloon on the exterior of the bite block 20 in order to provide additional room within the patient's mouth for tubes other than the catheter 40 (such as an oral gastric tube) or to avoid contact with injured regions within the patient's mouth. Another example is if it is desirable to maintain the balloon 32 inflated to prevent the device from being removed from the patient's mouth while the location of the catheter 40 is adjusted with the balloon 21 being at least partially deflated.

Depending upon the circumstances, a balloon may be used to perform just one of the functions described above in the preferred embodiment rather than both. For example, if the securing device is equipped with a mechanism other than a balloon for immobilizing the catheter 40 with respect to the securing device, the first portion 31 of the balloon 30 within the bite block 20 may be omitted, and the second portion 32 of the balloon 30 can be used solely to resist withdrawal of the securing device from a patient's mouth by means of the second portion 32 of the balloon 30. Alternatively, if it is undesirable to contact the interior of the patient's mouth due to trauma or inflammation, the second portion 32 of the balloon 30 on the exterior of the bite block 20 may be omitted, and the balloon 30 may be equipped with just the first portion 31 for restraining the catheter 40.

In another alternative embodiment, the bite block 20 includes a relatively soft (or flexible) material, such as a deformable plastic, rubber, sponge, or foam, to avoid damage to the patient's teeth if he/she bites into the bite block 20. Preferably, the soft material will reside in a groove around the circumference of the bite block 20. The soft material alternatively may be a coating/covering on at least a portion of the peripheral surface of the bite block 20.

Another alternative embodiment is to include bumps (or other protrusions) within the bore 21 of the bite block 20. Preferably, these bumps would provide some frictional resistance to movement of the catheter 40 relative to the bite block 20 and thus the securing device. These bumps preferably would line the bore 21 of the bite block 20. The bumps alternatively could instead be rubber or some other gripping material.

The means for resisting insertion of the entire device into the mouth of the patient corresponds to the various embodiments discussed above for the shield 10. The means for preventing occlusion of the catheter by the patient corresponds to the various embodiments discussed above for the bite block 20. The balloon 30 and its various embodiments are the corresponding structure for the means for gripping the catheter and means for selectively resisting removal of the device from the mouth of the patient. The means for allowing fluid to leave the mouth of the patient corresponds to the relief openings 12 discussed above.

One example of a method of using the securing device with a catheter 40 is as follows. Prior to intubation into a patient's airway, the catheter 40 preferably is passed through the shield 10 and the bite block 20 of the securing device, and the securing device is slid along the catheter 40 to near a proximal end of the catheter 40 and/or a location along the catheter 40 to provide an appropriate and desired depth upon insertion into the patient, which may be a human or an animal. Preferably, at this time, the balloon 30 is in a deflated state, so the securing device can easily slide along the catheter 40 in its lengthwise direction. The catheter 40 preferably is then inserted via the mouth into the patient's airway in a conventional manner to a position appropriate for the intended use of the catheter 40. Preferably, the bite block 20 is positioned between the patient's teeth (usually the incisors) and the shield 10 is at a desired location on the exterior of the patient's mouth, such as in a location contacting or in close proximity to the patient's lips. In this state, the balloon 30 is disposed on the intraoral region of the catheter 40, i.e., the region of the catheter 40 positioned within the patient's mouth. The balloon 30 preferably is then inflated through the inflating line 34. When inflated, the balloon 30 preferably expands within the patient's mouth to contact both the hard palate and lingual surface, thereby preventing inadvertent withdrawal of the securing device.

If it is desired to withdraw the securing device from the patient's mouth or to adjust the position of the securing device with respect to the catheter 40, the balloon 30 can be deflated, for example, by draining the fluid through the inflating line 34 with a suction force from the source of inflating fluid such as the syringe that was used to provide air, thereby enabling the securing device to be easily moved with respect to the patient's mouth and the catheter 40.

The preferred and alternative embodiments described above may be combined in a variety of ways with each other.

Those skilled in the art will appreciate that various adaptations and modifications of the preferred embodiments described above can be configured without departing from the scope and spirit of the invention. Therefore, it is to be understood that, within the scope of the appended claims, the invention may be practiced other than as specifically described herein.

What is claimed is:

1. A device for securing a catheter with respect to a patient's mouth comprising:
   a bite block having a distal end and a proximal end,
   a balloon attached to the distal end of said bite block, and within the patient wherein at least a portion of said balloon is inflatable within said bite block, and
   a shield extending from the proximal end of said bite block.

2. The device as claimed in claim 1, wherein at least a portion of said balloon is inflatable external to said bite block.

3. The device as claimed in claim 1, wherein said balloon has an oblong shape when inflated with a height greater than a width of said balloon.

4. The device as claimed in claim 1, wherein said balloon includes a passageway passing therethrough.

5. The device as claimed in claim 1, wherein said shield includes at least one means for allowing the insertion of medical instruments.

6. The device as claimed in claim 1, wherein said shield includes at least one relief opening.

7. The device as claimed in claim 1, wherein said bite block includes a cylinder passageway passing therethrough.

8. The device as claimed in claim 1, further comprising at least two hooks on opposing widthwise sides of said shield.

9. The device as claimed in claim 1, wherein said bite block includes a flexible material.

10. The device as recited in claim 9, wherein the flexible material includes one of rubber, sponge and foam.

11. An arrangement comprising:
   a catheter, and the securing device according to claim 1.

12. A device for securing a catheter with respect to a patient's mouth comprising:
   a bite block having a distal end and a proximal end,
   a balloon attached to the distal end of said bite block, said balloon including a first portion inflatable within said bite block to press against said catheter, and a second potion inflatable away from said distal end of said bite block, and
   a shield extending from the proximal end of said bite block.

13. A device for securing the catheter with respect to a patient's mouth comprising:
   a shield for positioning on an exterior of a patient's mouth for limiting a distance by which the securing device can be inserted into the patient's mouth and having an opening through which the catheter can pass;
   a bite block connected to the shield for insertion into the patient's mouth between the patient's teeth to protect the catheter against occlusion by the patient's teeth; and
   a balloon having a passageway through which the catheter can pass, a first portion disposed in the bite block, and a second portion disposed outside the bite block, the balloon having a deflated state in which the catheter may pass freely through the bite block and an inflated state in which the first portion of the balloon presses against the catheter to resist lengthwise movement of the catheter with respect to the bite block and the second portion can contact an interior surface of the patient's mouth to resist withdrawal of the securing device from a patient's mouth.

14. A method for intubating a patient through an oral cavity comprising:
   sliding a securing device having a balloon, a bite block, and a shield over a catheter to a point near a proximal end of the catheter,
   inserting a distal end of the catheter into the patient through the oral cavity,
   positioning the securing device such that the balloon is within the oral cavity of the patient, the bite block is between an upper jaw and a lower jaw of the patient, and the shield is external to the patient, and
   inflating the balloon such that is frictionally holds in place the catheter at a depth desired and fills a portion of the oral cavity such that the securing device will resist being removed from the patient.

15. The method according to claim 14, further comprising deflating the balloon when the catheter needs to be adjusted within the patient or removed from the patient.

16. A device for securing a catheter to a patient when the catheter is inserted into a mouth of the patient comprising:
   means for resisting insertion of the entire device into the mouth of the patient,
   means for preventing occlusion of the catheter by the patient,
   means for gripping the catheter, and
   means for selectively resisting removal of the device from the mouth of the patient.

17. The device according to claim 16, wherein said gripping means and said resisting removal means are integrally formed.

18. The device according to claim 16, wherein said resisting insertion means includes means for allowing the insertion of medical instruments.

19. The device according to claim 16, wherein said resisting insertion means includes means for allowing fluid to leave the mouth of the patient.

* * * * *